United States Patent
Liu et al.

(10) Patent No.: US 11,598,711 B2
(45) Date of Patent: Mar. 7, 2023

(54) METHOD AND APPARATUS FOR MEASURING STRESS DEPENDENCY OF SHALE PERMEABILITY WITH STEADY-STATE FLOW

(71) Applicant: ARAMCO SERVICES COMPANY, Houston, TX (US)

(72) Inventors: Hui-Hai Liu, Houston, TX (US); Jilin Zhang, Houston, TX (US); Jewel Duncan, Houston, TX (US)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 171 days.

(21) Appl. No.: 17/143,583

(22) Filed: Jan. 7, 2021

(65) Prior Publication Data
US 2022/0214262 A1    Jul. 7, 2022

(51) Int. Cl.
   *G01N 15/08*    (2006.01)
   *G01N 33/24*    (2006.01)

(52) U.S. Cl.
   CPC ..... *G01N 15/0826* (2013.01); *G01N 15/0806* (2013.01); *G01N 33/24* (2013.01)

(58) Field of Classification Search
   CPC .... G01N 15/00; G01N 15/08; G01N 15/0806; G01N 15/0826; G01N 33/24
   See application file for complete search history.

(56) References Cited

U.S. PATENT DOCUMENTS

| | | |
|---|---|---|
| 4,253,327 A | 3/1981 | Wiley |
| 5,544,520 A | 8/1996 | Graf et al. |
| 6,453,727 B1 | 9/2002 | Lenormand et al. |
| 10,401,274 B2 | 9/2019 | Liu et al. |

(Continued)

FOREIGN PATENT DOCUMENTS

| | | |
|---|---|---|
| CN | 104101564 B | 8/2016 |
| CN | 106290118 A | 1/2017 |

(Continued)

OTHER PUBLICATIONS

Liu, Hui Hai et al., "On the relationship between effective permeability and stress for unconventional rocks: Analytical estimates from laboratory measurements", Journal of Natural Gas Science and Engineering, ScienceDirect, Elsevier B.V., vol. 56, Jun. 2018, pp. 408-413 (6 pages).

(Continued)

*Primary Examiner* — Nguyen Q. Ha
(74) *Attorney, Agent, or Firm* — Osha Bergman Watanabe & Burton LLP

(57) ABSTRACT

A method for determining stress-dependent permeability includes providing a core sample in a pressurized core container of a testing apparatus and generating a steady-state flow of gas from an upstream reservoir in the testing apparatus along an axial direction through the pressurized core container into a downstream reservoir in the testing apparatus. During the steady-state flow, an inlet pressure at an inlet to the core sample, an outlet pressure at an outlet of the core sample, and a midpoint pressure at a midpoint of the core sample are measured. The stress-dependent permeability is calculated from a flow rate of the gas through the core sample and the measurements of the inlet pressure, the outlet pressure, and the midpoint pressure.

20 Claims, 3 Drawing Sheets

(56) References Cited

U.S. PATENT DOCUMENTS

| | | |
|---|---|---|
| 10,436,696 B2 | 10/2019 | Liu et al. |
| 10,571,384 B2 | 2/2020 | Liu et al. |
| 2016/0334322 A1 | 11/2016 | Ramakrishnan et al. |
| 2018/0372611 A1 | 12/2018 | Yue et al. |
| 2019/0234859 A1* | 8/2019 | Chen ................. E21B 49/08 |

FOREIGN PATENT DOCUMENTS

| | | | | |
|---|---|---|---|---|
| CN | 106872329 A | | 6/2017 | |
| CN | 107894383 A | | 4/2018 | |
| CN | 108458962 A | | 8/2018 | |
| CN | 109470617 A | | 3/2019 | |
| CN | 109900614 A | | 6/2019 | |
| CN | 110296921 A | * | 10/2019 | ......... G01N 15/0826 |
| CN | 110296921 A | | 10/2019 | |
| CN | 112730187 A | * | 4/2021 | ............ G01N 15/08 |
| JP | 3041417 B2 | | 5/2000 | |

OTHER PUBLICATIONS

Jones, S.C., "A Technique for Faster Pulse-Decay Permeability Measurements in Tight Rocks", SPE-28450-PA, SPE Form Eval, Society of Petroleum Engineers, vol. 12, Issue 1, Mar. 1997, pp. 19-25 (7 pages).

* cited by examiner

METHOD AND APPARATUS FOR MEASURING STRESS DEPENDENCY OF SHALE PERMEABILITY WITH STEADY-STATE FLOW

BACKGROUND

During hydrocarbon production, the pore pressure within an unconventional reservoir will decrease with time and thus the effective stress will also change accordingly as a function of time and location. Previous studies have indicated that permeability in an unconventional reservoir is sensitive to stress changes. The evolution of reservoir permeability owing to the stress change is used for predicting the hydrocarbon production from an unconventional reservoir and for managing the reservoir.

The dependency of permeability on stress is generally investigated in the laboratory. The current laboratory techniques for unconventional rock permeability measurement follow a "point-by-point" approach, which includes measuring one permeability data point for one test run, and multiple test runs to obtain a permeability-pressure curve. Thus, such approach is time consuming when trying to determine a permeability-pressure curve. The "point-by-point" approach uses laboratory techniques that are based on linearized gas flow theory requiring only small pore pressure disturbances to the experiment system.

Another methodology for investigating permeability is based on nonlinear gas flow theory for transient flow and allows for direct measurement of a permeability-pressure curve with a single test run involving transient flow through the core sample. However, this methodology has relatively strict requirements for the hardware of the system to produce accurate results. For example, it requires a close-to-zero dead volume for pressure transducers connected to a sample between the inlet and outlet of the sample and for the related connections. The dead volume is the space volume within the transducers and the related connections. A large dead volume will unfavorably disturb the transient flow process in the sample being tested.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to testing apparatuses that include a core container containing a core sample having an inlet, an outlet, and a pressure sensor positioned at a midpoint of the core sample, an upstream reservoir fluidly connected to the inlet of the core sample, an upstream pump connected to the upstream reservoir, a downstream reservoir fluidly connected to the outlet of the core sample, a downstream pump connected to the downstream reservoir, a confining pump connected to the core container, a flow meter positioned upstream of the inlet, an inlet pressure sensor positioned proximate the inlet of the core sample, and an outlet pressure sensor positioned proximate the outlet of the core sample.

In another aspect, embodiments disclosed herein relate to methods for determining stress-dependent permeability that include providing a core sample in a pressurized core container of a testing apparatus and generating a steady-state flow of gas from an upstream reservoir in the testing apparatus along an axial direction through the pressurized core sample into a downstream reservoir in the testing apparatus. During the steady-state flow, an inlet pressure at an inlet to the core sample, an outlet pressure at an outlet of the core sample, and a midpoint pressure at a midpoint of the core sample may be measured and used to calculate the stress-dependent permeability.

In yet another aspect, embodiments disclosed herein relate to methods for determining stress-dependent permeability that include loading a core sample into a core container that can be pressurized, generating a steady-state flow of gas through the core sample under a confining pressure, taking a plurality of measurements during the steady-state flow of gas through the core container, and calculating the stress-dependent permeability from the measurements of the inlet flow rate, the inlet pressure, the outlet pressure, and the midpoint pressure.

Other aspects and advantages will be apparent from the following description and the appended claims.

DETAILED DESCRIPTION

Embodiments disclosed herein relate generally to methods and apparatuses that utilize a steady-state flow condition to determine stress-dependent permeability of a core sample with a single test run. The derived permeability-stress function from a single test run may produce a permeability-stress curve that may be used, for example, for characterizing and modeling gas flow in a reservoir.

Methods and testing apparatuses of the present disclosure do not need a limited size of dead volumes because under the steady-state flow condition, the dead volumes (connected to the core sample) do not impact the flow process within the core sample. Further, methods and testing apparatuses disclosed herein allow for in-lab measurement of the permeability of a core sample as a function of pore pressure with a single test run. The results from the single in-lab test may be used to determine production characteristics of the formation from which the core sample was taken.

Figure 1:
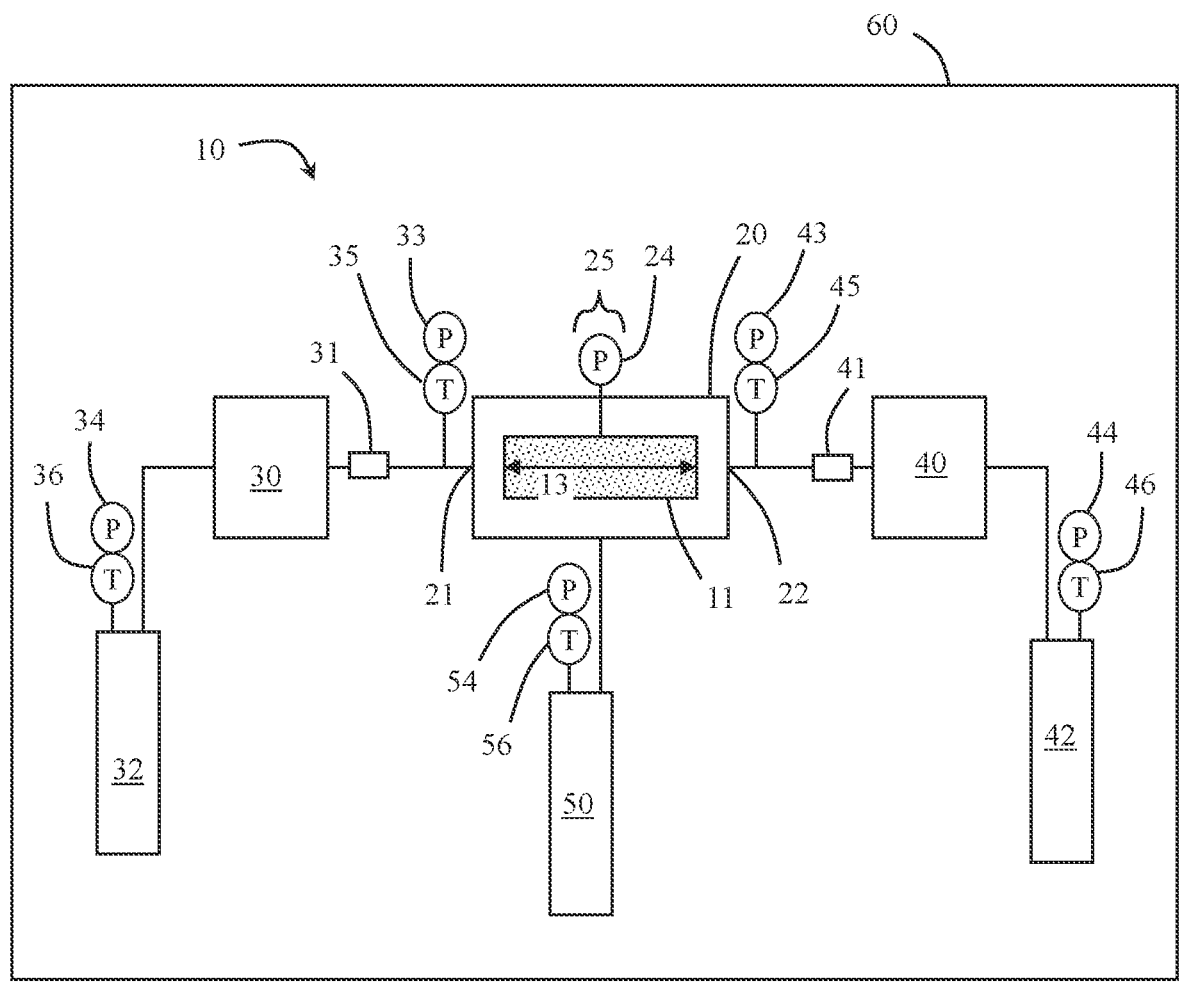
FIG. 1 shows a diagram of a testing apparatus according to embodiments of the present disclosure.

FIG. 1 shows an example of a testing apparatus 10 according to embodiments of the present disclosure, which takes different types of measurements during a single test run as fluid is flowed through a core sample 11. From the measurements, the permeability of the core sample 11 may be calculated as a function of pore pressure from the single test run. Generally, the testing apparatus 10 includes a core container 20 for holding the core sample 11, an upstream reservoir 30, and a downstream reservoir 40, which are each connected to three different pumps to provide confining pressure and fluid pressures, respectively.

The upstream reservoir 30 may be fluidly connected to an inlet 21 of the core container 20, which is fluidly connected to an inlet side of the core sample 11. Likewise, a downstream reservoir 40 may be fluidly connected to an outlet 22 of the core container 20, which is fluidly connected to an outlet side of the core sample 11. As used herein, the inlet side of the core sample 11 may be referred to as the core sample inlet, and the outlet side of the core sample 11 may be referred to as the core sample outlet. Further, the distance between the core container 20 inlet and the inlet side of the core sample may vary without affecting measurements and calculations according to embodiments of the present disclosure, as the flow path there between (e.g., a connecting tubing) has negligible flow resistance compared with flow in the core sample. Thus, measurements and calculations taken in accordance with methods disclosed herein may interchangeably refer to pressure measurements at the core container inlet and at the inlet side of the core sample as inlet 21. Similarly, because any flow path between the core container 20 outlet and the outlet side of the core sample would have negligible flow resistance compared with flow in the core sample, measurements and calculations taken in accordance with methods disclosed herein may interchangeably refer to pressure measurements at the core container outlet and at the outlet side of the core sample as the outlet 22.

The upstream reservoir 30 may be filled with a fluid, e.g., nitrogen gas. As used herein, a fluid may refer to a liquid or a gas unless stated otherwise. An upstream pump 32 may be connected to the upstream reservoir 30 to pump the fluid from the upstream reservoir 30 into the core sample 11. A downstream pump 42 may be connected to the downstream reservoir 40 to pump fluid between the core sample 11 and the downstream reservoir 40, where the downstream reservoir 40 may be used to collect the fluid flowing out of the core sample 11 and/or to provide a back pressure to the outlet 22 of the core sample 11.

The upstream pump 32 and downstream pump 42 may be, for example, a hydraulic pump or other pump having high accuracy and high resolution, and may include precise pressure and flowrate control and measurement (e.g., have a flow meter, pressure sensor, and/or temperature sensors incorporated). The upstream pump 32 and the downstream pump 42 may together be used to control fluid flow through the core sample 11, including the pressure and flow rate of the fluid through the core sample 11. Flow meters 31, 41 may be positioned upstream the inlet 21 and downstream the outlet 22, respectively, to measure the mass flow rates at the inlet 21 and outlet 22 of the core sample 11. In some embodiments, the upstream pump 32 and/or the downstream pump 42 may be provided with a flow meter to measure the flow rates from the respective pumps.

A confining pump 50 may be connected to the core container 20 to apply a confining pressure around the core sample 11. For example, the core sample 11 may be placed in a sample cell, which may surround the core sample 11 by an enclosed sleeve having an inlet in fluid communication with the inlet 21 of the core sample 11 and an outlet in fluid communication with the outlet 22 of the core sample. The enclosed core sample 11 may be positioned within the core container 20, such that fluid may be flowed from the upstream reservoir 30 through the enclosed core sample 11. The confining pump 50 may pump a confining fluid (e.g., a water-based fluid, an oil-based fluid, or gas) into the core container 20 around the enclosed core sample 11.

Further, a plurality of pressure sensors may be used to monitor the pressure conditions at different locations in the testing apparatus 10 during the test. Pressure sensors may include high accuracy pressure transducers known in the art, including for example, piezoelectric pressure sensors, strain gauge pressure transducers, capacitance pressure transducers, and potentiometric pressure transducers.

For example, an inlet pressure sensor 33 may be positioned at or proximate the inlet 21 of the core sample 11, an outlet pressure sensor 43 may be positioned at or proximate the outlet 22 of the core sample 11, and a midpoint pressure sensor 24 may be positioned at an approximate midpoint 25 of the core sample 11. In some embodiments, the midpoint 25 may be designated as a region large enough to fit the pressure sensor 24 that is halfway between the axial length between the inlet 21 and outlet 22 of the core sample.

The midpoint pressure sensor 24 may be positioned along the core sample 11 to measure pore pressure in the core sample 11 at approximately the middle of the core sample 11 along its flow length 13. The flow length 13 of the core sample 11 is measured along the dimension of the core sample 11 parallel to the direction of the flow of fluid through the core sample 11 during testing. For example, when fluid is flowed through an axial length of a core sample 11 during testing, the flow length 13 of the core sample 11 is the axial length of the core sample 11. In the embodiment shown, the core sample 11 may be axially aligned between the inlet 21 and outlet 22 of the core container 20 to where, during testing, fluid may flow from the inlet 21, through the axial dimension of the core sample 11 (the flow length 13), and out the outlet 22 of the core container 20. In some embodiments, the midpoint pressure sensor 24 may be positioned at the midpoint 25 of the core sample 11.

The midpoint pressure sensor 24 may contact the core sample 11 and include one or more of a communication line or a transmitter to transmit a midpoint pressure reading. For example, midpoint pressure readings may be transmitted to a computer program for deriving a permeability-stress function from the test.

Pump pressure sensors 34, 54, 44 may also be provided on each of the upstream pump 32, confining pump 50, and downstream pump 42, respectively, to measure the pressures of the pumps.

The testing apparatus 10 may also include a plurality of temperature sensors to monitor the temperature conditions at different locations of the testing apparatus 10 during the test. For example, an inlet temperature sensor 35 may be positioned at or proximate to the inlet 21 of the core sample, an outlet temperature sensor 45 may be positioned at or proximate to the outlet 22 of the core sample, and/or pump temperature sensors 36, 56, 46 may be provided on each of the upstream pump 32, confining pump 50, and downstream pump 42, respectively, to measure the temperature of the pumps during operation.

The whole testing apparatus 10 may be placed in an oven 60 with a constant temperature such that permeability measurement tests may be conducted in an isothermal condition. In some embodiments, the oven 60 may be set to a temperature corresponding with a downhole temperature of a formation of interest, from which the core sample 11 was taken. During a permeability measurement test, pressures at the inlet 21, outlet 22, and the approximate middle 25 of a core sample 11 and the flow rate across the core sample 11 may be measured after a steady-state flow is established through the core sample 11 and under the temperature conditions of the oven 60.

Figure 2:
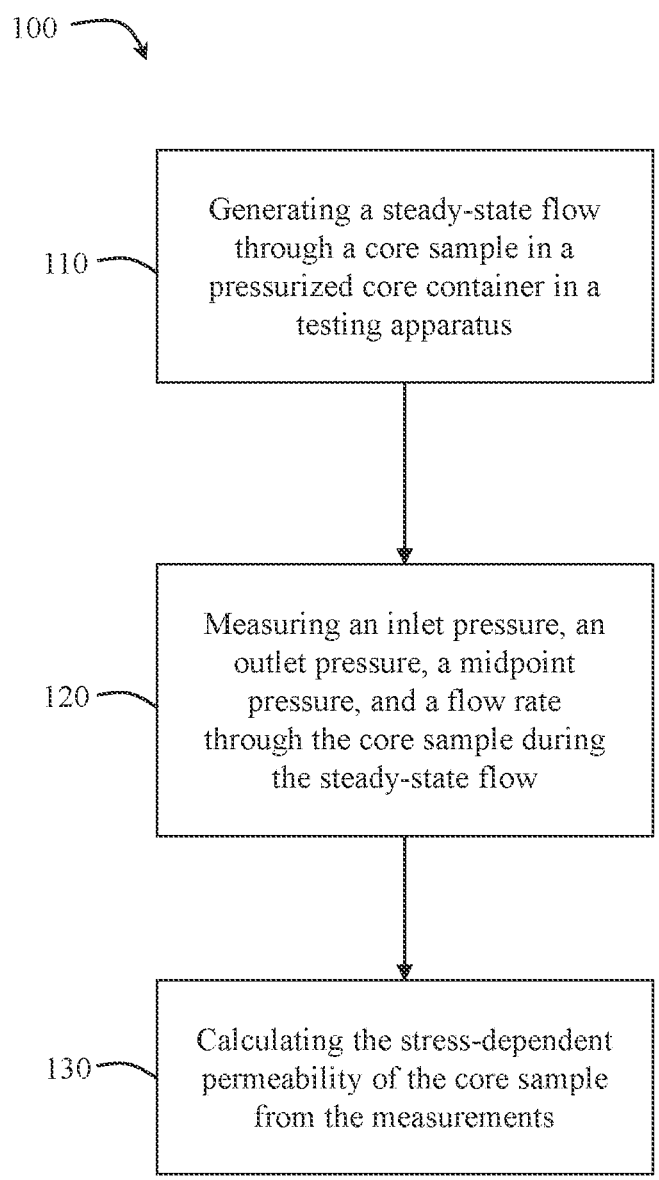
FIG. 2 shows a method according to embodiments of the present disclosure.

FIG. 2 shows an example of a method 100 for determining stress-dependent permeability in a core sample using a testing apparatus according to embodiments of the present disclosure. The method 100 may include the steps of generating a steady-state flow through a core sample in a pressurized core container in a testing apparatus, such as shown in FIG. 1 (step 110), measuring an inlet pressure, an outlet pressure, a midpoint pressure, and a flow rate through the core sample during the steady-state flow (step 120), and calculating the stress-dependent permeability of the core sample from the measurements (step 130). The testing apparatus may be in an oven at a constant temperature during generating the steady-state flow and measuring.

Core samples used in testing methods disclosed herein may be collected from an unconventional reservoir and may include, for example, a shale sample, a limestone sample, or a sandstone sample. For example, core samples may be collected from a coring process that includes sending a coring tool downhole to drill and collect a core sample from the downhole location. The core sample may be brought to the surface of the well and sent to a lab for conducting the permeability measurement tests disclosed herein. The drilled core samples may have a cylindrical shape having a diameter ranging between, for example, 1 to 2 inches (e.g., 1.5 inches). In some embodiments, the core samples may be cut to have axial lengths, for example, ranging from about 1 to 2 inches long. However, other core sample sizes may be used depending on the size of the testing apparatus. Further, in preparation for the permeability measurement tests, water, hydrocarbons, and other fluids included from the coring process may be removed from the core samples prior to a permeability measurement test.

A core sample may be provided in a pressurized core container for a permeability measurement test. For example, a core sample may be sleeved with different sheet layers (so the fluid flowing through the sample and the confining fluid are separated by the sleeves) and placed in a core container. A confining pump may be used to introduce a confining fluid into and around the sleeved core sample and to continue to flow confining fluid through the core container after the core container containing the core sample is filled with confining fluid to ensure there is no gas remaining inside of the core container. For example, confining fluid may be injected into a bottom side of the core container to fill the core container with the confining fluid, while the incoming confining fluid may expel air in the core container at a top side of the core container. The confining fluid and the sleeved core sample in the filled core container may be locked-in to the core container after no air is present in the core container. A confining pressure may then be applied to the core sample using the confining pump, e.g., by pumping more confining fluid to the space between the sleeved core sample and the core container. For example, after cell-confining is locked in, a confining pressure (e.g., ranging between 400 psi to 600 psi) may be applied around the sleeved core sample to reduce the possibility of leaking.

Referring to step 110 of the method shown in FIG. 2, after a sleeved core sample is provided in a pressurized core container (e.g., core container 20 in FIG. 1) of a testing apparatus, a steady-state flow of gas through the core sample may be generated to flow from an upstream reservoir in the testing apparatus along an axial direction through the core sample into a downstream reservoir in the testing apparatus. The steady-state flow of gas may be generated using an upstream pump in the testing apparatus to pump the gas from the upstream reservoir into the inlet of the core sample and a downstream pump in the testing apparatus to pump the gas from the outlet of the core sample to the downstream reservoir. Thus, three separate pumps may be used to generate the steady-state flow of gas, including the upstream pump and the downstream pump to flow fluid through the core sample and a confining pump to apply a confining pressure to the core sample as fluid is flowed through.

In one example of generating a steady-state flow, a sleeved core sample may be provided in a pressurized core container having a confining pressure of 500 psi applied to the core sample. A fluid pore pressure of 2,500 psi may then be slowly imposed (e.g., by gradually increasing the pressure at a selected rate of pressure build up) using both the upstream and downstream pumps fluidly connected to the core sample through the upstream and downstream reservoirs while the confining pressure is also slowly raised up in sync with the pore pressure such that the confining pressure remains 500 psi higher than the pore pressure. The fluid pore pressure of 2,500 psi may be used to minimize the impact of diffusion on permeability measurements. As the fluid is introduced into the core sample, the confining pressure may increase simultaneously to maintain a 500 psi differential pressure (the difference between the confining pressure and the pore pressure). The use of the extra 500 psi or higher confining pressure may ensure good sealing of the core sample. Pressure equilibrium within the core sample may not be needed for this step.

Inlet pressure (fluid pressure in the inlet of the core container) may be increased using the upstream pump by several thousand psi to cover the range of effective stress (confining pressure minus pore pressure) that is of interest in a formation, and may then be kept constant after raising the confining pressure to a predetermined amount (higher than maximum value of the inlet pressure). The outlet pressure (fluid pressure in the outlet of the core container) may also be kept constant through the downstream pump. In such manner, fluid may flow from the inlet to the outlet of the core sample because the inlet pressure is higher than the outlet pressure. During the fluid flow, mass flow rates from the upstream and downstream pumps may be measured. Steady-state flow may be achieved when the relative difference between the upstream and downstream flow rates is less than 1%, where the relative difference is defined as the difference between inlet and outlet flow rates divided by the inlet flow rate.

In step 120, during the steady-state flow, measurements may be taken of the fluid within the testing apparatus, including an inlet pressure $p_i$ at or near an inlet to the core sample, an outlet pressure $p_o$ at or near an outlet of the core sample, a midpoint pressure $p_x$ at or around the midpoint of the core sample, and a flow rate Q of the fluid into the core sample (inlet flow rate).

For a steady-state flow test, the fluid pressure at the inlet of core sample (or in the upstream reservoir) $p_i$ and fluid pressure at the outlet of the core sample (or in the downstream reservoir) $p_o$ shall be kept as constant. The fluid pressure of the upstream reservoir and the fluid pressure measured at or near the inlet of the core sample may be used interchangeably as the inlet pressure $p_i$ because the flow resistance between the upstream reservoir and core sample inlet is negligible compared to the flow resistance within the core sample. Similarly, the fluid pressure of the downstream reservoir and the fluid pressure measured at or near the outlet of the core sample may be used interchangeably as the outlet pressure $p_o$ because the flow resistance between the downstream reservoir and core sample outlet is negligible compared to the flow resistance within the core sample.

In step 130, the stress-dependent permeability may then be calculated from the flow rate of the gas through the core sample and the pressure measurements of the inlet pressure, the outlet pressure, and the midpoint pressure.

When steady-state flow is achieved along the core sample, the mass flow rate Q will be independent of time and location and is given by Darcy's law:

$$Q = -A \frac{k\rho}{\mu} \frac{\partial p}{\partial x} \qquad \text{Eq. 1}$$

where A is the area of the core sample's cross section, k is permeability of the core sample, ρ and μ are fluid density and viscosity, respectively, p is fluid pressure, and x is the spatial coordinate along the core sample's flow length with a zero value at the inlet side of the core sample and an L value at the outlet side of the core sample.

Integrating Eq. 1 from the inlet side (x=0) of the core sample to a location at $x=L_x$ (the position of the midpoint pressure transducer, approximately at the middle of the core sample) yields:

$$\int_0^{L_x} Q dx = -A \int_{p_i}^{p_x} \frac{k\rho}{\mu} dp \quad \text{Eq. 2}$$

where $p_i$ is inlet pressure at the inlet of the core container and $p_x$ is the midpoint pressure at $x=L_x$. For a steady-state flow process, Q is constant. Thus, Eq. 2 may be rewritten as:

$$\frac{QL_x}{A} = \int_{p_x}^{p_i} \frac{k\rho}{\mu} dp \quad \text{Eq. 3}$$

Previous studies have demonstrated that permeability in an unconventional formation is an exponential function of effective stress (confining pressure minus pore pressure). Thus, for a constant confining pressure, Eq. 3 can be rewritten in terms of pore pressure as:

$$k = k_o \exp[\alpha(p-p_0)] \quad \text{Eq. 4}$$

where $k_o$ is the outlet permeability at the outlet side of the core sample, $p_o$ is the outlet pressure at the outlet of the core container, and α is the stress sensitivity parameter for permeability. The stress dependency of permeability is determined by two constant parameters $k_o$ and α. Thus, embodiments of the present disclosure may include determining two constant parameters $k_o$ and α based on laboratory measurements.

Using the sequence of Equations 5-7, below, the stress sensitivity parameter α may be solved from Equations 1, 3 and 4, above, using the measured inlet pressure $p_i$ of the core sample, the measured outlet pressure $p_o$ of the core sample, the measured midpoint pressure $p_x$ of the core sample, and the measured flow rate Q of the fluid into the core sample.

Inserting Eq. 4 into Eq. 3 gives:

$$\frac{QL_x}{A} = k_o \int_{p_x}^{p_i} \frac{\exp[\alpha(p-p_o)]\rho dp}{\mu}. \quad \text{Eq. 5}$$

Similarly, integrating Eq. 1 from the inlet side of the core sample (x=0) to the outlet side of the core sample (x=L) results in:

$$\frac{QL}{A} = k_o \int_{p_0}^{p_i} \frac{\exp[\alpha(p-p_o)]\rho dp}{\mu}. \quad \text{Eq. 6}$$

Dividing Eq. 5 by Eq. 6 gives $$\frac{L}{L_x} = 1 + \frac{\int_{p_o}^{p_x} \frac{\exp[\alpha(p-p_o)]\rho dp}{\mu}}{\int_{p_x}^{p_i} \frac{\exp[\alpha(p-p_o)]\rho dp}{\mu}}. \quad \text{Eq. 7}$$

From Equation 7, the only unknown is parameter α. The inlet pressure $p_i$, the midpoint pressure $p_x$, and the outlet pressure $p_o$ are measured from the permeability test. The fluid density ρ and fluid viscosity μ are known for a given fluid (e.g., nitrogen gas) used for the permeability test.

After estimating the stress sensitivity parameter α, the outlet permeability $k_o$ at the outlet of the core sample may be calculated by:

$$k_o = \frac{\frac{QL}{A}}{\int_{P_o}^{p_i} \frac{\exp[\alpha(p-p_o)]\rho dp}{\mu}} \quad \text{Eq. 8}$$

where the flow rate Q is measured under the steady-state flow condition.

As discussed above, Equations 7 and 8 may be used for determining the two constant parameters, the outlet permeability $k_o$ at the outlet side of the core sample and stress sensitivity parameter α for permeability. As shown in Equation 4, the outlet permeability $k_o$ at the outlet side of the core sample and stress sensitivity parameter α for permeability may be used to determine the relationship between permeability and pore pressure under a given confining pressure used in the permeability test. The effective stress on the formation is equal to the confining pressure minus pore pressure.

According to embodiments of the present disclosure, the calculated stress-dependent permeability may be used to predict a formation permeability of a formation under a formation confining pressure different from the lab test confining pressure in the pressurized core container. If the confining pressure in a formation of interest is different from the confining pressure used in the laboratory test, the permeability can be calculated using the following relationship:

$$k = k_o \exp[-\alpha(\sigma-\sigma_o)] \quad \text{Eq. 9}$$

where σ is the effective stress of the formation of interest (i.e., formation confining pressure minus pore pressure), $\sigma_o$ is the effective stress at the outlet side of the core sample under the laboratory conditions (i.e., test confining pressure minus outlet pressure measured in the laboratory test), and parameters a and $k_o$ remain the same as those determined above. Equation 9 may be reduced to Equation 4 for a fixed confining pressure.

According to embodiments of the present disclosure, a computer programming language (e.g., MatLab, Simulink) may be used to solve any or all of Equations 1-9, presented above. In some embodiments, a computer program may be used to automate some or all of the testing and calculating steps for determining the stress dependent permeability of a formation of interest. For example, in some embodiments one or more of the temperature sensors, pressure sensors, and flow meters used in a testing apparatus disclosed herein may automatically send measurements to be inputted into a computer program, where the computer program may calculate the stress dependent permeability of the core sample being tested based on Equations 1-9 and the measurements taken during testing.

In some embodiments, a measured inlet pressure $p_i$, a measured midpoint pressure $p_x$, a measured outlet pressure $p_o$, the known fluid density ρ and fluid viscosity μ of the fluid used in testing for different pore pressures, the flow length L of the core sample being tested, the midpoint location $L_x$ of the pressure sensor in the core sample being measured, a measured steady-state flow rate Q, and the area of core sample cross section A may be inputted into a computer program. Based on the given inputs, the computer program may calculate the pore pressure dependent permeability of the core sample using Equation 4. The stress sensitivity parameter α may be determined using Equation 7 based on the inputted data. After the stress sensitivity parameter α is determined, the outlet permeability $k_o$ at the outlet pressure may be determined with Equation 8.

An example method performed in the lab is described below, demonstrating that (1) the stress sensitivity parameter α and outlet permeability $k_o$ can be accurately determined and (2) typical errors in pressure measurements have insignificant impacts on the estimated parameter values when using methods according to embodiments of the present disclosure.

In the example experiment, a 2 inch long core sample with a diameter of 1 inch was cored from a formation of interest and brought to the surface for testing. The core sample was loaded into a core container of a testing apparatus according to embodiments of the present disclosure. The testing apparatus included an inlet pressure sensor at the inlet of the core sample, an outlet pressure sensor at the outlet of the core sample, and a midpoint pressure sensor at a midpoint location along the core sample of $L_x$=1 inch. For the experiment, the core sample had known true values for the stress sensitivity parameter, α=2.50E-4 $psi^{-1}$, and the outlet permeability, $k_o$=200 nD. The test was performed at 50° C. and with nitrogen gas as the working fluid to measure permeability.

The inlet pressure of the gas was increased to an initial inlet pressure using an upstream pump in the testing apparatus, and the outlet pressure was held at an initial outlet pressure using a downstream pump in the testing apparatus. To generate a steady-state flow of gas through the core sample, the upstream pump pumped gas from an upstream nitrogen reservoir into the inlet of the core container, and the downstream pump was used to control an outlet flow rate of the nitrogen gas out of the outlet of the core container with a downstream nitrogen reservoir. If a relative difference between the inlet flow rate and the outlet flow rate was greater than 1 percent, the pumping rate of the gas into or out of the core sample was adjusted until the steady-state flow was generated through the core sample.

During the steady-state flow of gas, the inlet pressure was gradually increased to a final inlet pressure of 5,000 psi, and the outlet pressure was held at 2,500 psi, where the final inlet pressure and outlet pressure were maintained while taking the measurements for permeability testing and calculating. The final inlet pressure was selected to be greater than a range of effective stress pressures in the formation of interest.

Meanwhile, a confining pressure was applied within the core container using a confining pump fluidly connected to the core container. The confining pressure was increased while increasing the inlet pressure to maintain a constant pressure differential between the inlet pressure at the inlet of the core sample and the confining pressure in the core container.

During the steady-state flow of gas through the core sample, a plurality of measurements were taken, including measuring a flow rate Q through the core sample, measuring the inlet pressure $p_i$ at the inlet to the core sample, measuring the outlet pressure $p_o$ at the outlet of the core sample, and measuring a midpoint pressure $p_x$ at the midpoint ($L_x$=1 inch) of the core sample, where Q=4.54E-7 kg/s, $p_i$=5,000 psi, $p_o$=2,500 psi, and $p_x$=4,032.5 psi. From the measurements taken during the test, the stress-dependent permeability was then calculated using computational computing software.

The stress sensitivity parameter, a, was calculated using the stress sensitivity equation (Equation 7):

$$\frac{L}{L_x} = 1 + \frac{\int_{p_o}^{p_x} \frac{\exp[\alpha(p-p_o)]\rho dp}{\mu}}{\int_{p_x}^{p_i} \frac{\exp[\alpha(p-p_o)]\rho dp}{\mu}}$$

where the measured inlet pressure $p_i$ was 5,000 psi, the measured midpoint pressure $p_x$ was 4,032.5 psi, the measured outlet pressure $p_o$ was 2,500 psi, the length of the core sample L was 2 inches, the midpoint distance $L_x$ was 1 inch, and the density ρ and viscosity μ of nitrogen gas at the testing temperature and pressure was known. From using the measurements in the stress sensitivity equation (Equation 7), the stress sensitivity parameter, a, was calculated as α=2.51E-4 $psi^{-1}$, which is approximately the same as the true value α=2.50E-4 $psi^{-1}$.

The outlet permeability, $k_o$, of the core sample at the outlet pressure 2,500 psi was calculated using the outlet permeability equation (Equation 8):

$$k_o = \frac{\frac{QL}{A}}{\int_{p_o}^{p_i} \frac{\exp[\alpha(p-p_o)]\rho dp}{\mu}}$$

where the measured flow rate Q was 4.54E-7 kg/s, and the cross-sectional area of the core sample A was $\pi(1\ inch/2)^2$. From using the measurements in the outlet permeability equation (Equation 8), the outlet permeability, $k_o$, was calculated as $k_o$=199.80 nD, which is approximately the same as the true value $k_o$=200 nD.

Depending on the type of pressure sensors used, the precision of the pressure measurement may vary (e.g., the precision of a pressure transducers may be less than 1 psi). To validate that pressure measurement errors would not significantly impact the stress sensitivity parameter α and outlet permeability $k_o$ parameter estimations, the above calculations from the experiment were redone, keeping all the test conditions and measurements the same except the midpoint pressure $p_x$ was adjusted by 1 psi greater than and 1 psi less than the measured midpoint pressure (4,032.50 psi). The estimated parameter values of the stress sensitivity parameter $\alpha_{est}$ and outlet permeability $k_{o-est}$ using the adjusted midpoint pressures ($n_{x-est}$=4,032.50 psi+1 psi and $n_{x-est}$=4,032.50 psi−1 psi) were then compared with the true values of the stress sensitivity parameter α and outlet permeability $k_o$. The relative errors of these parameters, defined as the difference between estimated parameter values ($\alpha_{est}$ and $k_{o-est}$) and true parameter values (a and 10 divided by the true parameter values (α and $k_o$), were less than 0.8%.

The same process was used with adjusted inlet pressures ($p_{i-est}$=1 psi greater than the measured value and $p_{i-est}$=1 psi less than the measured value) and with adjusted outlet pressures (n=1 psi greater than the measured value and $p_{o-est}$=1 psi less than the measured value) to calculate estimated parameter values of the stress sensitivity parameter $\alpha_{est}$ and outlet permeability $k_{o-est}$ using the adjusted inlet and outlet pressures. The estimated parameter values of the stress sensitivity parameter $\alpha_{est}$ and outlet permeability $k_{o\text{-}est}$ were then compared with the true values of the stress sensitivity parameter $\alpha$ and outlet permeability $k_o$, where the upper limit of the calculated relative errors was 0.8%. Because this error limit is negligible, it was shown that methods according to embodiments of the present disclosure may robustly estimate the parameter values (stress sensitivity parameter $\alpha$ and outlet permeability 10 within measurement precision variances.

Thus, methods according to embodiments of the present disclosure may produce both accurate and robust estimates of the stress sensitivity parameter $\alpha$ and outlet permeability $k_o$ of a core sample being tested.

Figure 3:
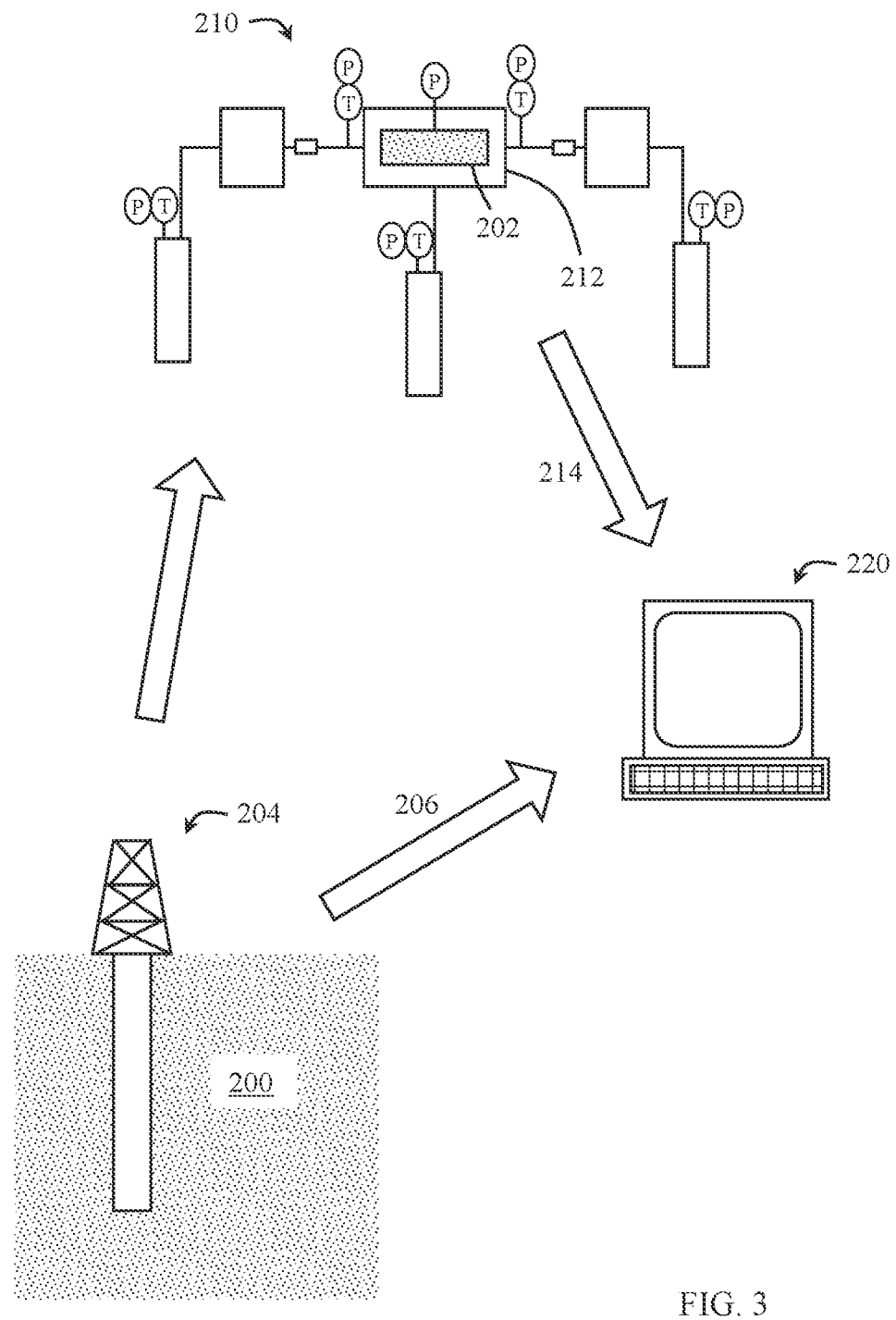
FIG. 3 shows a diagram of a system according to embodiments of the present disclosure.

Upon determining a stress sensitivity parameter $\alpha$ and outlet permeability $k_o$ of a core sample from a formation of interest, the determined stress sensitivity parameter $\alpha$ and outlet permeability $k_o$ may be used to estimate the permeability of the formation. For example, FIG. 3 shows a schematic representation of methods for estimating the permeability of a formation 200 of interest.

A core sample 202 may be taken from a well 204 in the formation 200 of interest, for example, in a coring operation. The core sample 202 may then be loaded into a testing apparatus 210 according to embodiments of the present disclosure. The stress-dependent permeability relationship of the core sample 202 may be determined by taking pressure measurements along the core sample 202 under a steady-state flow test run. For example, as described above, a steady-state flow of gas may be generated through the core sample 202 in a pressurized core container 212, under a test confining pressure, in the testing apparatus 210. An inlet pressure $p_i$, an outlet pressure $p_o$, a midpoint pressure $p_x$, a flow rate Q through the core sample 202, and optionally other measurements may be measured during the steady-state flow test run.

The measurements from the test run may be inputted into a computing system 220. The computing system 220 may include an input (e.g., keyboard, mouse, touchscreen), an output (e.g., screen, audio output), memory, including short-term memory (e.g., random access memory (RAM)) and long-term memory (e.g., a hard drive), and one or more processors. Software instructions for receiving and processing the measurements 214 from the test run may be stored and/or accessed through the computing system 220. The software instructions may include Equations 1-9, provided above, and instructions for inputting the collected measurement data into the Equations. Results of the calculations may be outputted to a user and/or may be used as input(s) to estimate the permeability of the formation 200 from which the core sample was taken.

To estimate the permeability of the formation 200 from which the core sample 202 was taken, the permeability, k, of the core sample 202 under the test confining pressure, p, may be calculated using the permeability equation (Equation 4):

$$k = k_o \exp[\alpha(p - p_o)].$$

When the formation 200 is under a formation confining pressure that is the same as the test confining pressure, p, the formation 200 may be estimated to have the same permeability as the calculated permeability, k, of the tested core sample 202. When the formation 200 is under a formation confining pressure different from the test confining pressure, the formation permeability, $k_f$, may be predicted using a formation permeability equation (Equation 9):

$$k_f = k_o \exp[-\alpha(\sigma - \sigma_0)]$$

wherein $\sigma$ is a formation effective stress, the formation effective stress being equal to the formation confining pressure minus a pore pressure of the formation, and wherein $\sigma_o$ is an effective stress of the core sample proximate to the outlet (test confining pressure minus the outlet pressure measured during testing).

The formation permeability equation may be inputted into a reservoir simulator to predict hydrocarbon production from a reservoir in the formation 200, the reservoir simulator comprising at least one computer implemented software application with instructions to simulate the reservoir on a computer.

During hydrocarbon production from an unconventional reservoir, the pore pressure may decrease with time, and thus, effective stress of the formation may change with time, as well. In this case, permeability will be a function of both time and location as a result of stress alteration during the production from the formation. Using methods according to embodiments of the present disclosure, the stress dependent permeability of the formation may be calculated from a measured inlet pressure $p_i$, a measured midpoint pressure $p_x$, a measured outlet pressure $p_o$, and a measured flow rate Q collected from a single test run of a core sample. The determined stress dependent permeability may then be used as an input into a reservoir simulator to predict the hydrocarbon production from the reservoir. Because the measured stress dependency captures the permeability evolution during production, the reservoir simulator may simulate production characteristics based on the changing permeability over time, which may be derived from the stress dependent permeability methods disclosed herein.

Methods and apparatuses disclosed herein may provide a way to determine a stress-dependent permeability function of a core sample using a single test under steady-state flow, thereby increasing measurement efficiency by multiple times, compared with conventional methods for determining a stress-dependent permeability function.

For example, in conventional methods, a steady state flow across a core sample for a given stress may be established, and then a single permeability data point for the given stress may be determined. After that, the stress condition may be changed, and the test procedure is repeated to obtain a second permeability data point for the second given stress. Following the same way, many test runs may be conducted to obtain a permeability vs. stress curve (stress-dependent permeability function) that consists of multiple points, each of which corresponds to a test run.

In contrast, methods and testing apparatuses according to embodiments of the present disclosure may be used to determine the permeability vs. stress curve (stress-dependent permeability function) with a single test run. Thus, using the same amount of time it takes for conventional methods to measure a single data point, an entire permeability vs. stress curve may be determined from a single test run according to embodiments of the present disclosure. For example, if 5 data points are measured from a conventional method to characterize a permeability vs. stress curve, the permeability vs. stress curve may be determined using methods disclosed herein in 20% (⅕) of the experiment time used by that conventional method. In such manner, methods according to embodiments of the present disclosure may provide a significant improvement over conventional methods.

While the present disclosure has been described with respect to a limited number of embodiments, those skilled in the art, having benefit of this disclosure, will appreciate that other embodiments may be devised which do not depart from the scope of the disclosure as described herein. Accordingly, the scope of the disclosure should be limited only by the attached claims.

What is claimed:

1. A testing apparatus, comprising:
a core container containing a core sample comprising:
an inlet;
an outlet; and
a pressure sensor positioned at a midpoint of the core sample;
an upstream reservoir fluidly connected to the inlet of the core sample;
an upstream pump connected to the upstream reservoir;
a downstream reservoir fluidly connected to the outlet of the core sample;
a downstream pump connected to the downstream reservoir;
a confining pump connected to the core container;
at least one flow meter;
an inlet pressure sensor positioned proximate the inlet of the core sample; and
an outlet pressure sensor positioned proximate the outlet of the core sample.

2. The apparatus of claim 1, further comprising a temperature sensor positioned proximate the inlet and the outlet of the core sample.

3. The apparatus of claim 1, wherein the at least one flow meter is provided on at least one of the upstream pump and the downstream pump.

4. The apparatus of claim 1, wherein a temperature sensor and a pressure sensor is provided on each of the upstream pump, the downstream pump, and the confining pump.

5. The apparatus of claim 1, wherein the at least one flow meter is positioned downstream of the outlet of the core sample.

6. A method for determining stress-dependent permeability, comprising:
providing a core sample in a pressurized core container of a testing apparatus;
generating a steady-state flow of gas from an upstream reservoir in the testing apparatus along an axial direction through the core sample into a downstream reservoir in the testing apparatus;
during the steady-state flow, measuring an inlet pressure at an inlet to the core container, an outlet pressure at an outlet of the core container, and a midpoint pressure at a midpoint of the core sample; and
calculating the stress-dependent permeability from a flow rate of the gas through the core sample and the measurements of the inlet pressure, the outlet pressure, and the midpoint pressure.

7. The method of claim 6, wherein providing the core sample in the pressurized core container comprises:
wrapping at least one sleeve around the core sample;
loading the sleeved core sample into a sample cell in the core container;
using a confining pump to introduce a confining fluid into the core container;
continuing to flow confining fluid through the sample cell after the sample cell containing the core sample is filled with confining fluid;
locking the confining fluid and the core sample in the filled sample cell; and
applying a confining pressure to the sample cell using the confining pump.

8. The method of claim 6, wherein an upstream pump in the testing apparatus pumps the gas from the upstream reservoir into the inlet of the core sample and a downstream pump in the testing apparatus pumps the gas from the outlet of the core sample to the downstream reservoir.

9. The method of claim 6, wherein the testing apparatus is in an oven at a constant temperature during generating the steady-state flow and measuring.

10. The method of claim 6, further comprising using the stress-dependent permeability to predict a formation permeability of a formation under a formation pressure different from a confining pressure in the pressurized core container.

11. A method for determining stress-dependent permeability, comprising:
loading a core sample into a core container;
generating a steady-state flow of gas through the core sample under a confining pressure;
taking a plurality of measurements during the steady-state flow of gas through the core container, comprising:
measuring a flow rate through the core sample;
measuring an inlet pressure at an inlet to the core sample;
measuring an outlet pressure at an outlet of the core sample; and
measuring a midpoint pressure at a midpoint of the core sample; and
calculating the stress-dependent permeability from the measurements of the inlet flow rate, the inlet pressure, the outlet pressure, and the midpoint pressure.

12. The method of claim 11, wherein generating the steady-state flow of gas comprises:
using an upstream pump to pump gas from an upstream reservoir into the inlet of the core sample;
using a downstream pump to control the outlet pressure of the gas out of the outlet of the core sample into a downstream reservoir; and
wherein a relative difference between an inlet flow rate and an outlet flow rate is less than 1 percent.

13. The method of claim 12, further comprising increasing the inlet pressure of the gas to an initial inlet pressure using the upstream pump.

14. The method of claim 13, further comprising:
applying the confining pressure within the core container using a confining pump fluidly connected to the core container; and
increasing the confining pressure while increasing the inlet pressure to maintain a constant pressure differential between the inlet pressure at the inlet of the core sample and the confining pressure in the core container.

15. The method of claim 11, wherein after generating the steady-state flow of gas, further comprising:
increasing the inlet pressure to a final inlet pressure, wherein the difference between the confining pressure and final inlet pressure is greater than a selected range of effective stress pressures of interest; and
maintaining the final inlet pressure while taking the plurality of measurements.

16. The method of claim 11, further comprising determining a stress sensitivity parameter, a, using a stress sensitivity equation:

$$\frac{L}{L_x} = 1 + \frac{\int_{p_o}^{p_x} \frac{\exp[\alpha(p-p_o)]\rho dp}{\mu}}{\int_{p_x}^{p_i} \frac{\exp[\alpha(p-p_o)]\rho dp}{\mu}}$$

where $p_i$ is the inlet pressure, $p_x$ is the midpoint pressure, $p_o$ is the outlet pressure, $\rho$ is a density of the gas, $\mu$ is a viscosity of the gas, L is a length of the core sample, and $L_x$ is a midpoint distance from the inlet to the midpoint.

17. The method of claim 16, further comprising determining an outlet permeability, $k_o$, of the core sample at the outlet pressure using an outlet permeability equation:

$$k_o = \frac{\frac{QL}{A}}{\int_{p_o}^{p_i} \frac{\exp[\alpha(p-p_o)]\rho dp}{\mu}}$$

where Q is the flow rate measured during the steady-state flow of gas, and A is a cross-sectional area of the core sample.

18. The method of claim 17, further comprising calculating a permeability, k, of the core sample at the confining pressure, p, using a permeability equation:

$$k = k_o \exp[\alpha(p-p_o)].$$

19. The method of claim 18, further comprising predicting a formation permeability $k_f$ of a formation under a formation pressure different from the confining pressure, using a formation permeability equation:

$$k_f = k_o \exp[-\alpha(\sigma-\sigma_o)]$$

wherein $\sigma$ is a formation effective stress, the formation effective stress being equal to the formation pressure minus a pore pressure of the formation; and wherein $\sigma_o$ is an effective stress of the core sample proximate to the outlet, the effective stress being equal to the confining pressure minus the outlet pressure.

20. The method of claim 18, further comprising inputting the permeability equation into a reservoir simulator to predict a hydrocarbon production from a reservoir, the reservoir simulator comprising at least one computer implemented software application with instructions to simulate the reservoir on a computer.

* * * * *